US006766651B2

(12) United States Patent
Dillenback (10) Patent No.: US 6,766,651 B2
(45) Date of Patent: Jul. 27, 2004

(54) CENTRAL MEDIA DISPENSER FOR USE IN HVAC SYSTEM

(76) Inventor: Scott Dillenback, 100 Briarwood Ct., New Hartford, NY (US) 13413

( * ) Notice: Subject to any disclaimer, the term of this patent is extended or adjusted under 35 U.S.C. 154(b) by 0 days.

(21) Appl. No.: 10/425,100

(22) Filed: Apr. 28, 2003

(65) Prior Publication Data

US 2003/0230091 A1 Dec. 18, 2003

Related U.S. Application Data

(63) Continuation-in-part of application No. 09/796,177, filed on Feb. 28, 2001, now Pat. No. 6,553,777.

(51) Int. Cl.[7] ............................. F25D 17/00; F28D 3/00; F28C 1/00; F24F 3/00; G01F 11/00
(52) U.S. Cl. ............................. 62/180; 62/121; 62/179; 62/208; 62/78; 62/171; 126/113; 222/1
(58) Field of Search ........................... 62/171, 121, 179, 62/208, 78; 126/113; 222/1

(56) References Cited

U.S. PATENT DOCUMENTS

| | | |
|---|---|---|
| 3,140,147 A | 7/1964 | Neuwald et al. |
| 3,178,255 A | 4/1965 | Neuwald et al. |
| 3,510,252 A | 5/1970 | Reich |
| 4,229,415 A | 10/1980 | Bryson |
| 4,617,157 A | 10/1986 | Stein et al. |
| 4,742,475 A | 5/1988 | Kaiser et al. |
| 4,752,422 A | 6/1988 | Uchida et al. |
| 4,913,034 A | 4/1990 | Ripple et al. |
| 5,029,729 A | 7/1991 | Madsen et al. |
| 5,078,046 A | 1/1992 | Mascolo et al. |
| 5,186,869 A | 2/1993 | Stumpf et al. |
| 5,240,487 A | 8/1993 | Kung |
| 5,382,410 A | 1/1995 | Peltier |
| 5,494,644 A | 2/1996 | Thomas et al. |
| 5,607,651 A | 3/1997 | Thomas et al. |
| 5,720,176 A | 2/1998 | Manson et al. |
| 5,724,256 A * | 3/1998 | Lee et al. .................... 700/285 |
| 5,805,768 A | 9/1998 | Schwartz et al. |
| 5,924,597 A | 7/1999 | Lynn |
| 6,553,777 B2 | 4/2003 | Dillenback |

* cited by examiner

Primary Examiner—William Doerrler
Assistant Examiner—Filip Zec
(74) Attorney, Agent, or Firm—August E. Roehrig, Jr.; Hancock & Estabrook (57) ABSTRACT

A user-programmable monitoring and dispensing system for controlling the dispensing of water vapor and various other media into an HVAC air stream in residential or commercial structures. The various media to be dispensed are preferably water-soluble, and mixed with the system water supply to be dispensed with the water vapor added to the HVAC air stream. These

CENTRAL MEDIA DISPENSER FOR USE IN HVAC SYSTEM

REFERENCE TO RELATED APPLICATION

This is a continuation-in-part of application Ser. No. 09/796,177, filed Feb. 28, 2001 by the present inventor, now U.S. Pat. No. 6,553,777.

BACKGROUND OF THE INVENTION

1. Field of the Invention

This invention relates in general to a dispensing system for use in a heating, ventilating or air conditioning (HVAC) air stream and, in particular, to a central or zoned forced air HVAC media dispensing system for dispensing water vapor and/or other water soluble air-flow borne materials.

More specifically, but without restriction to the particular embodiment and/or use which is shown and described herein for purposes of illustration, this invention relates to a user-programmable central or zoned HVAC dispensing system for introducing various media such as water vapor, fragrances or other air-treating materials to improve living and working environments. Further, the invention of this application relates to dispensing systems for HVAC applications wherein the individual user may selectively shift the range of concentrations of media according to the level of concentration perceived by the user.

2. Description of Related Technology

The use of a humidification device for a central or zoned forced air HVAC system to improve living and working environments is known to those skilled in this art. Such systems generally comprise either passive evaporation of water from a reservoir adjacent to the HVAC air stream, or a circulating liquid retaining medium which passes in an endless path of movement through a water bath positioned within the HVAC air stream. While such systems are somewhat effective and simple, they are generally activated when an air stream is moving through the HVAC system and do not provide precise user control. If it is desired to dispense an additional medium into the air stream, the additional medium is manually added to the bath for dispensing into the air flow. Such systems consequently have wide variations in the amount of the media dispensed into the air stream which changes as the concentration of the media being dispensed varies, such as by evaporation, as well as the conditions of the ambient air.

In the parent of the present application there is provided a media dispensing system for use in HVAC applications including a central processor providing, in response to user-programmable data entry, control signals to a dispensing system for discharging a quantity of media into the air stream of the HVAC system. The media is supplied, also in accordance with user-selected inputs, from a plurality of media reservoirs to a manifold wherein the media is diluted to a level of concentration selected by the user through the data entry. The user may choose from a plurality of concentrations, e.g., five levels from lowest to highest, and the central processor controls discharge valves to provide the proper amount of media to the dilution manifold for the selected concentration. The central processor is programmed with a concentration algorithm specifying the amount of media corresponding to each selected level of concentration. For example, for user-selected concentrations or intensities of media, the proportions of media to water may be 1.3%, 3%, 5%, 10% and 20% for low, medium low, medium, medium high and high, respectively. However, there is no means for making the media concentration less than 1.3% or greater than 20% should the user desire lower or higher concentrations than those established by the concentration algorithm which is pre-programmed in the central processor.

SUMMARY OF THE INVENTION

It is therefore an object of this invention to improve central and zoned dispensing systems for dispensing materials into a HVAC air stream.

Another object of this invention is to provide a range of user-programmable operational controls for the dispensing of materials into an HVAC air stream.

A further object of this invention is to provide a user-programmable central dispensing system for dispensing and monitoring the dispensing of one or more water-soluble materials into the air stream of an HVAC system in a predetermined and programmable quantity.

A more particular object of the present invention is to provide a system for dispensing media into the air stream of an HVAC system which offers the user a greater degree of control over the concentration or intensity of the media at various specified concentration levels.

These and other objects are attained in accordance with the present invention wherein there is provided a user-programmable monitoring and dispensing system for controlling the dispensing of water vapor and various other media into an HVAC air stream in residential or commercial structures. The various media to be dispensed are preferably water-soluble, and mixed with the system water supply to be dispensed with the water vapor added to the HVAC air stream. These materials may be fragrances or aromas, intended to produce an aesthetic effect, or they can be agents capable of pesticidal, bacteriacidal, fungicidal or sporacidal effect for use as acute or prophylactic treatment for infestation.

Among the user inputs is the desired concentration or intensity (which words are used interchangeably herein) of the media in the water solution. The user may choose from, for example, five concentration levels, denoted low, medium low, medium, medium high and high. The central processor is programmed with a concentration algorithm which establishes the actual percentage of media in the solution at each level. However, particularly when the dispensed media is a fragrance, one user may perceive the concentration at the level established by the processor to be lower or higher than another user, based on their individual sense of smell and preference for the particular fragrance being dispensed. In fact, the user may prefer a concentration, at least at certain times, which is lower than the concentration at the lowest selectable level, or higher than the highest level. The present invention addresses, and successfully solves, this problem by permitting the user to change the concentration algorithm after being exposed to the concentration at the default (original) setting for a predetermined time.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

These and additional embodiments of the invention may now be better understood by referring to the following detailed description of the invention wherein the illustrated embodiment is described.

DETAILED DESCRIPTION OF THE INVENTION

Throughout this description, the preferred embodiment and examples shown should be considered as exemplars, rather than limitations on the apparatus and methods of the present invention.

Figure 1:
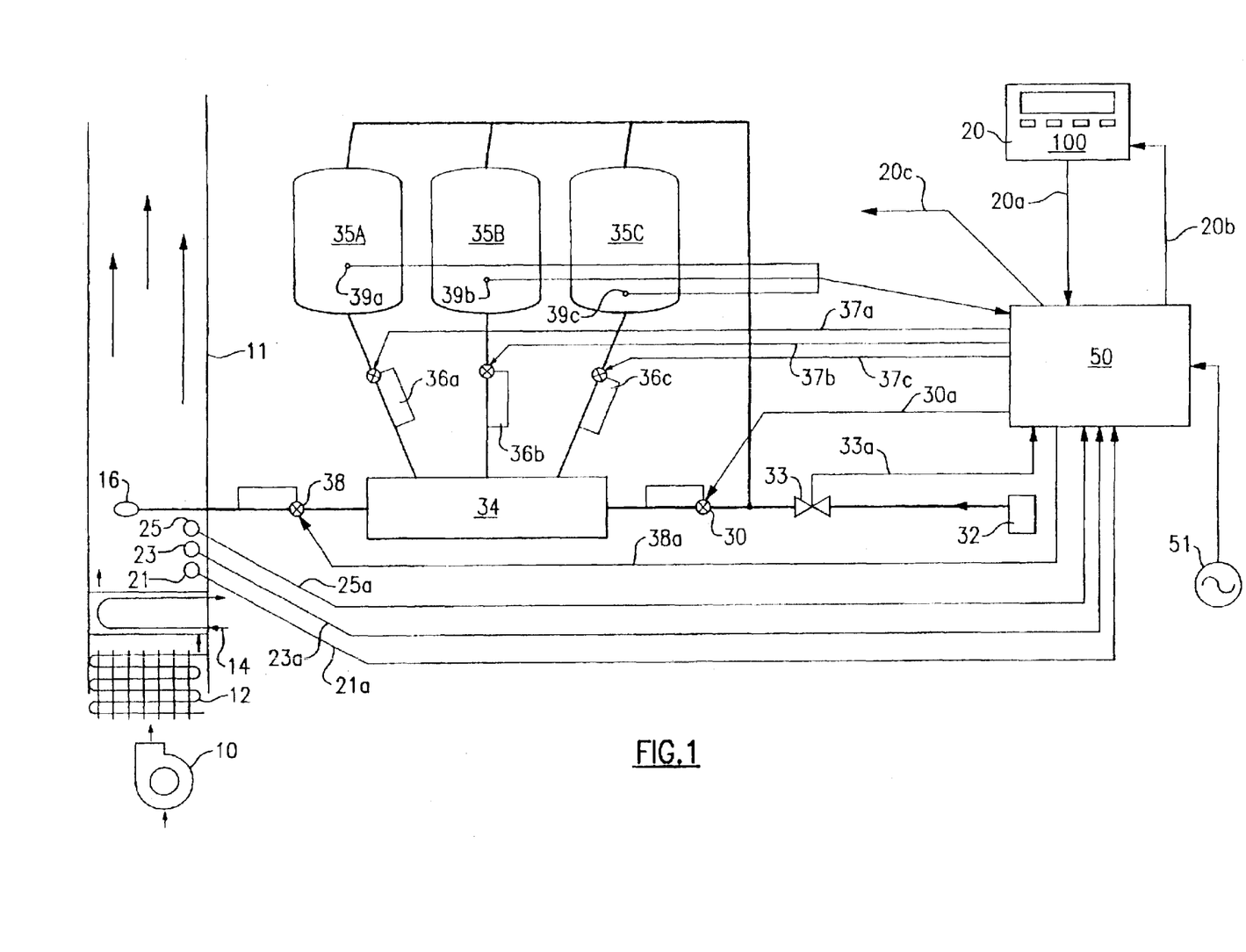
FIG. 1 is a mechanical schematic of a preferred embodiment of the dispensing system to better illustrate the components thereof and the manner in which such components interrelate in the system operation.

Referring now to the drawings, there is illustrated in FIG. 1 the various air flow components of an HVAC system and the central dispensing system of this invention. The portion of the HVAC system illustrated includes an air movement generating device, such as a blower 10 which generates an air stream which pass through duct work 11 to a desired residential or commercial space. The HVAC system includes a heat exchanger 12 positioned in the air stream path to heat the air moving through the duct 11 in response to the temperature set by a HVAC thermostat controller 20, the input of which is entered through a user operated keypad/display unit 100. In addition, an A/C coil 14 is positioned in the air stream to cool the temperature thereof in response to the temperature programmed through the thermostat 20. The blower 10, duct work 11, heat exchanger 12 and A/C coil 14 are standard components utilized in HVAC forced air systems. Positioned down stream from the blower 10, heat exchanger 12 and A/C coil 14, in the direction of air movement, is a pressure or flow sensor 21, such as available from Sensotec Inc., 2080 Arlingate Lane, Columbus, Ohio 43228, a humidity sensor 23 and a temperature sensor 25, such as a HE-6310 Series Duct-mount humidity/temperature sensor, available from Johnson Controls, Inc., 507 East Michigan Street, Milwaukee, Wis. 53202, all of which are connected to a system central processor 50, such as an Intel Type 8051 Microcontroller DS89C420-QCS Dallas Semiconductor Ultra High Speed 8051 Based Microcontroller PLCC Package available from Newark Electronics, 3 Marcus Boulevard, Albany, N.Y. 12205-1129, for providing air stream sensor inputs as to the air movement, moisture content of the air stream and the air stream temperature to the system central processor. Further down stream from these sensors, is a dispenser 16 which may be in the form of an ultrasonic transducer, available from Keramos Advanced Piezoelectrics, 5460 W. 84th Street, Indianapolis, Ind. 46268 and Etalon Innovative Piezo Transducers, P.O. Box 127, Lebanon, Ind. 46052, or vaporizer through which water vapor and/or water-soluble materials, available from AromaTech Co., 130 Industrial Parkway, Somerville, N.J. 088076, are dispensed into the HVAC air stream in response to a user-defined program input to the system central processor 50 by means of the keypad/display unit 100, such as a Type XK-5LC or Type LCD-96M Multi Menu Keypad available from FBII, 149 Eileen Way, Soyosset, N.Y. 11791-5316 or JDS Technologies, 12200 Thatcher Ct., Poway, Calif. 92064-6876. While a single dispenser 16 is illustrated, it is to be understood that a single dispensing head may be utilized as illustrated or multiple dispensing heads may be utilized with each one of the multiple dispensing heads being connected by means of a dilution manifold to each individual media reservoir. The dispensing heads may be piezo-electric ultrasonic transducers, atomizer spray nozzles or a media saturated evaporation wick. The dispenser 16, as illustrated in FIG. 1, is shown dispensing into the main plenum of an HVAC system for a centralized effect from the medium dispensed. However, it is to be understood that separate dispensers may be utilized in various trunk ducts as well as the central plenum for dispersal of the medium into specific locations serviced by the HVAC system.

Figure 2:
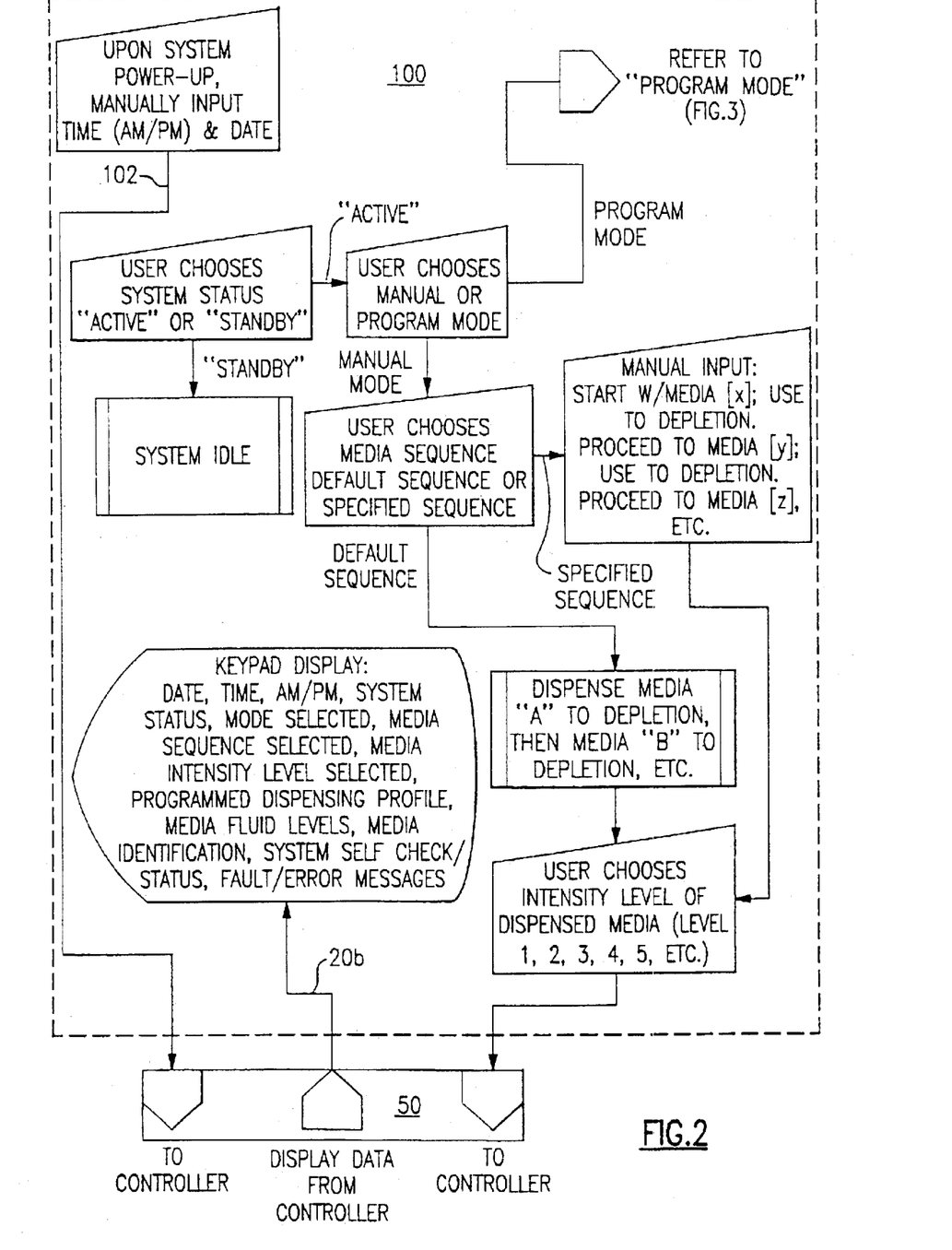
FIG. 2 is a logic block diagram of the system operation.

The display/HVAC thermostat portion 20 of the keypad/display unit 100 is coupled to the system central processor 50 to provide the inputs illustrated in FIG. 2 to control the heating/cooling operation of the system central processor 50.

The system central processor 50 is connected to a suitable standard power supply 51 to provide power to the unit upon start up. At this time a thermostat control signal is sent 20c from the system central processor 50 to actuate one or more of the blower 10, heat exchanger 12, or A/C coil 14, in response to an on/off signal determined from the thermostat setting.

Figure 3:
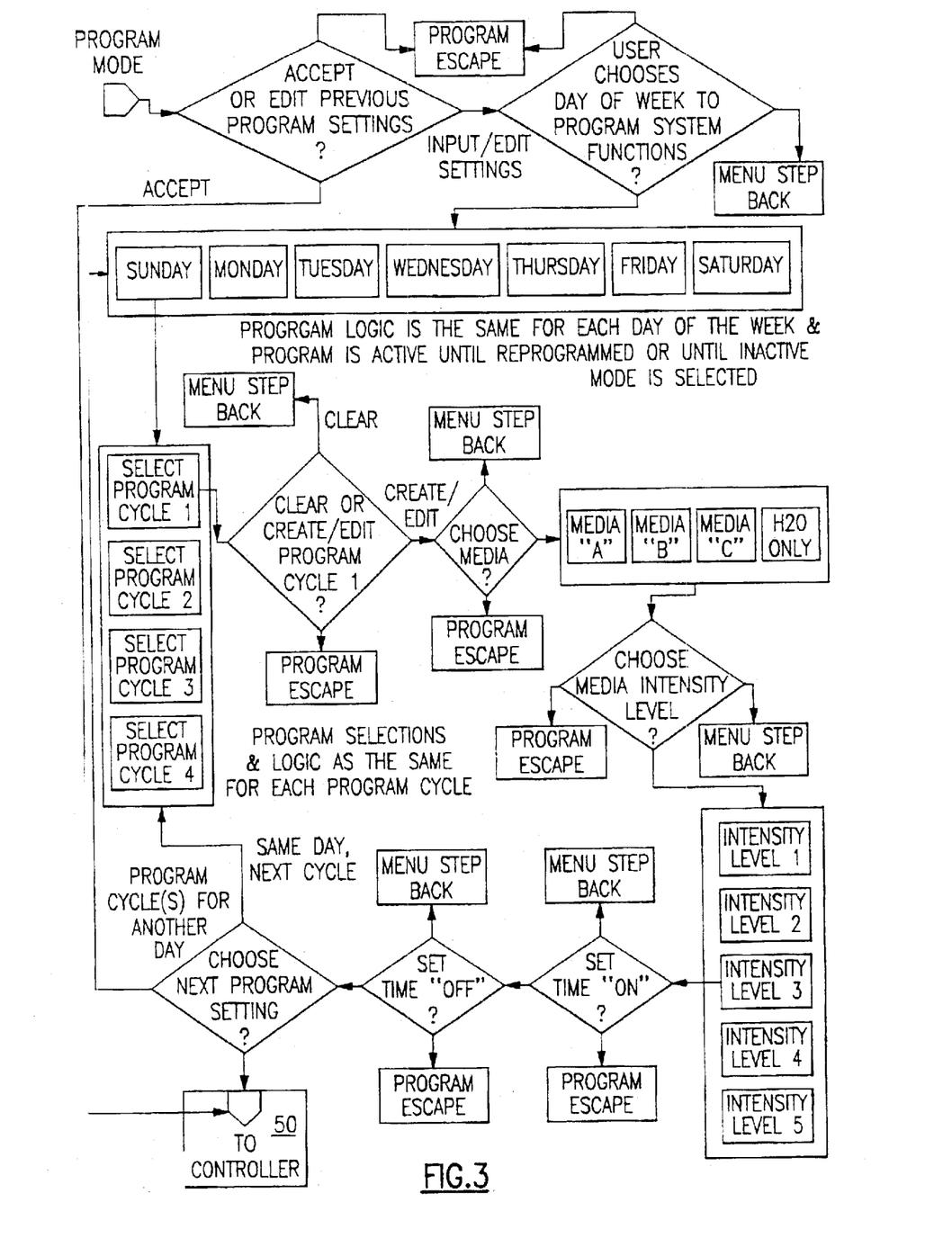
FIG. 3 is a logic block diagram of the operation of the user interface keypad/display through which the system is programmed.

The system central processor 50 is programmed in the manner illustrated in FIG. 3, to control the operation of the media dispensing system on a daily basis, to control the dispensing of a selected medium or media, and to control the intensity thereof during the programmed cycle. The system operation, in response to the user-defined program inputs, and the output from various component sensors used in controlling system operations, are controlled in the manner illustrated in FIG. 4.

Referring again to FIG. 1, the input from the user-defined program keypad/display unit 100, including the thermostat signal, is coupled 20a to the system central processor 50 and appropriate display information is coupled 20b from the system central processor 50 back to the keypad/display 100 to confirm that the signals input from the keypad/display unit 100 have been received and processed by the system central processor 50. While in the preferred embodiment disclosed herein as the best mode contemplated by the inventor for practicing the invention the keypad/display unit 100 is utilized, it is to be understood that the input coupled 20a to the dispenser system central processor 50 could be from a home automation control system commonly used to network and integrate the control and function of several subsystems in the space being controlled, with the feedback 20b from the system central processor 50 being coupled to such an automation control system instead of a keypad/display unit 100. A suitable home automation control system, not shown, has been found to be an Omni, Omni LT, and Omni Pro models available from Home Automation, Inc., 5725 Powell Street, Suite A, New Orleans, La. 70123.

When the HVAC system is in operation, an input 21a will be received from the pressure or flow sensor 21 to the system central processor 50 confirming the movement of the air stream in the duct 11, and input signals will be received 23a from the humidity sensor 23 and from the temperature sensor 25 to provide input 25a to the system central processor 50 as to the moisture content and the temperature of the air stream moving through the duct 11. This information will be processed through the system central processor 50 and control 30a the operation of a water intake control valve 30, available from South Bend Controls, 1237 Northside Boulevard, South Bend, Ind. 46615; HydraForce, Inc., 500 Barclay Boulevard, Lincolnshire, Ill. 60069; and Deltrol Controls, 2740 South 20th Street, Milwaukee, Wis. 53215, through which water passes from a suitable municipal or domestic supply source 32 into a dilution manifold 34 wherein water soluble media to be dispensed into the air stream are added for dilution prior to dispensing.

The water from water supply 32 is also connected to one parameters are input to the system central processor 50 is illustrated in FIG. 3.

If the user chooses to operate the system in a "Program" mode; whereby individual medium and intensity parameters can be selected and set for individual days of the week, the user selects the "Program" option when the system "Active" display is presented.

Referring to FIG. 3, upon entering the "Program" mode the user is instructed to either accept or edit a previous program setting. If at this time the user elects not to enter the "Program" mode, an "Escape" instruction is provided which returns the user to the "Active" display whereby the system may be operated in the "Manual" mode or the user may return the system to the "Standby" mode. If, however, the user elects to proceed with the "Program" mode, the user must either "Accept" the previous program settings (or the factory settings if this is an initial installation) or select the "Edit" option if it is desired to make changes in the program previously entered. Throughout the operation in the "Program" mode, an "Escape" option is available to enable the user to return to the "Active" input level thereby cancelling all instructions entered to that point and the system returning to the previous program settings, or a "Menu Step Back" option is also available to permit the user to correct an entry error without losing the settings previously entered.

Upon selecting the "Edit" option, the user sequentially selects each day of the week to define the parameters of operation of the system for that day. These parameters include the time of program operation, identified as "Cycle 1", "Cycle 2", "Cycle 3" and "Cycle 4". These times of operation are set for each day and may be individually accepted as presented previously, or edited. After the program cycle is selected, the particular medium, water vapor only or one of the media 35a, 35b, 35c which is to be dispensed, maybe chosen. The intensity level (concentration) of the selected medium which is to be dispensed may be selected as well as the time period selected for operation during the program cycle can be chosen and entered through the keyboard/display unit 100 into the system central processor 50. This information is sequentially entered into the system central processor 50 through the keypad/display unit 100 for each day of the week.

Figure 5:
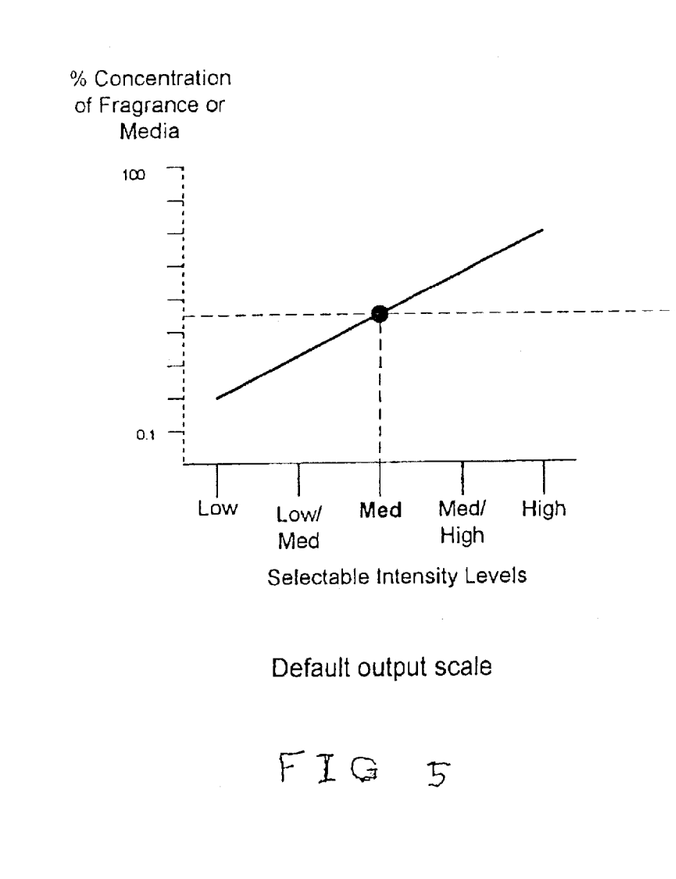
FIGS. 5 and 5A are graphs illustrating the default and user calibrated output scales, respectively, of the concentration algorithm.

Although the system described above allows the user to choose from a plurality of concentration levels for each of a plurality of media, the percentage of media in the dispensed solution remains the same for each level any time the system is in use. For example, "Media A" may have a concentration of 1.3% at the "Low" setting and 20% at the "High" setting. Thus, if the user wants a concentration of Media A which is less than 1.3% or greater than 20%, this cannot be achieved with the system as described to this point. This is illustrated by the graph of FIG. 5, providing an example of the concentration algorithm, a line of constant slope, for Media A. The concentration algorithm and percentages of media at each of five intensity levels are as follows:

| User-selectable intensity levels: | Low | MedLow | Med | MedHi | High |
| --- | --- | --- | --- | --- | --- |
| Media A dilution algorithm | 0.5(0.5 * X) | 0.5 * X | X | 2 * X | 2(2 * X) |
| Default value | 1.3% | 3% | 5% | 10% | 20% |

Figure 5A:
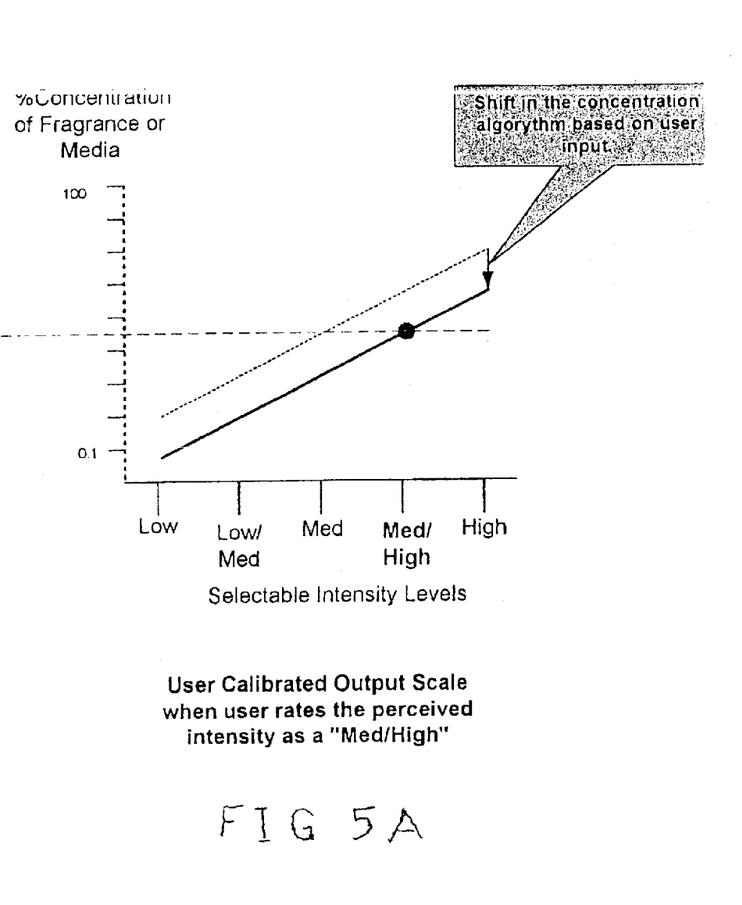

In the user calibration procedure of the present invention, the above algorithm is in effect when Media A is recognized by the central processor as the medium in use. At system startup, the default value at the medium intensity level, i.e., 5%, is automatically chosen. The medium, assumed in this case to be a fragrance, is dispensed at this level for a predetermined time period, e.g., one hour. At the end of that time, the display prompts the user to enter the intensity level which most closely corresponds to the user's perception of the intensity of fragrance at that time. If the user's sense of smell and personal preference for the fragrance indicate that the intensity level is in the medium-high range, the user presses the "Med/High" button on the data entry/display 100. Doing so resets the dilution scale by relocating the default X value on the algorithm. That is, the concentration algorithm is shifted from the position shown by the dotted line in FIG. 5A (i.e., the position of FIG. 5) to the solid line position of FIG. 5A. The concentration of media is reduced at each of the five selectable intensity levels.

Using the example above, if the user rates the perceived intensity as:

| | Low | Med/Low | Med | Med/High | High |
| --- | --- | --- | --- | --- | --- |
| 1. High, then the resulting user-calibrated scale, for that specific fragrance would become: | 0.31% | 0.63% | 1.25% | 2.50% | 5% |
| 2. Med/High, then the resulting user-calibrated scale, for that specific fragrance would become: | 0.63% | 1.25% | 3% | 5% | 10% |
| 3. Med, then the resulting user-calibrated scale, for that specific fragrance would become: | 1.25% | 2.5% | 5% | 10% | 20% |
| 4. Med/Low, then the resulting user-calibrated scale, for that specific fragrance would become: | 2.5% | 5% | 10% | 20% | 40% |
| 5. Low, then the resulting user-calibrated scale, for that specific fragrance would become: | 5% | 10% | 20% | 40% | 80% |

Figure 6:
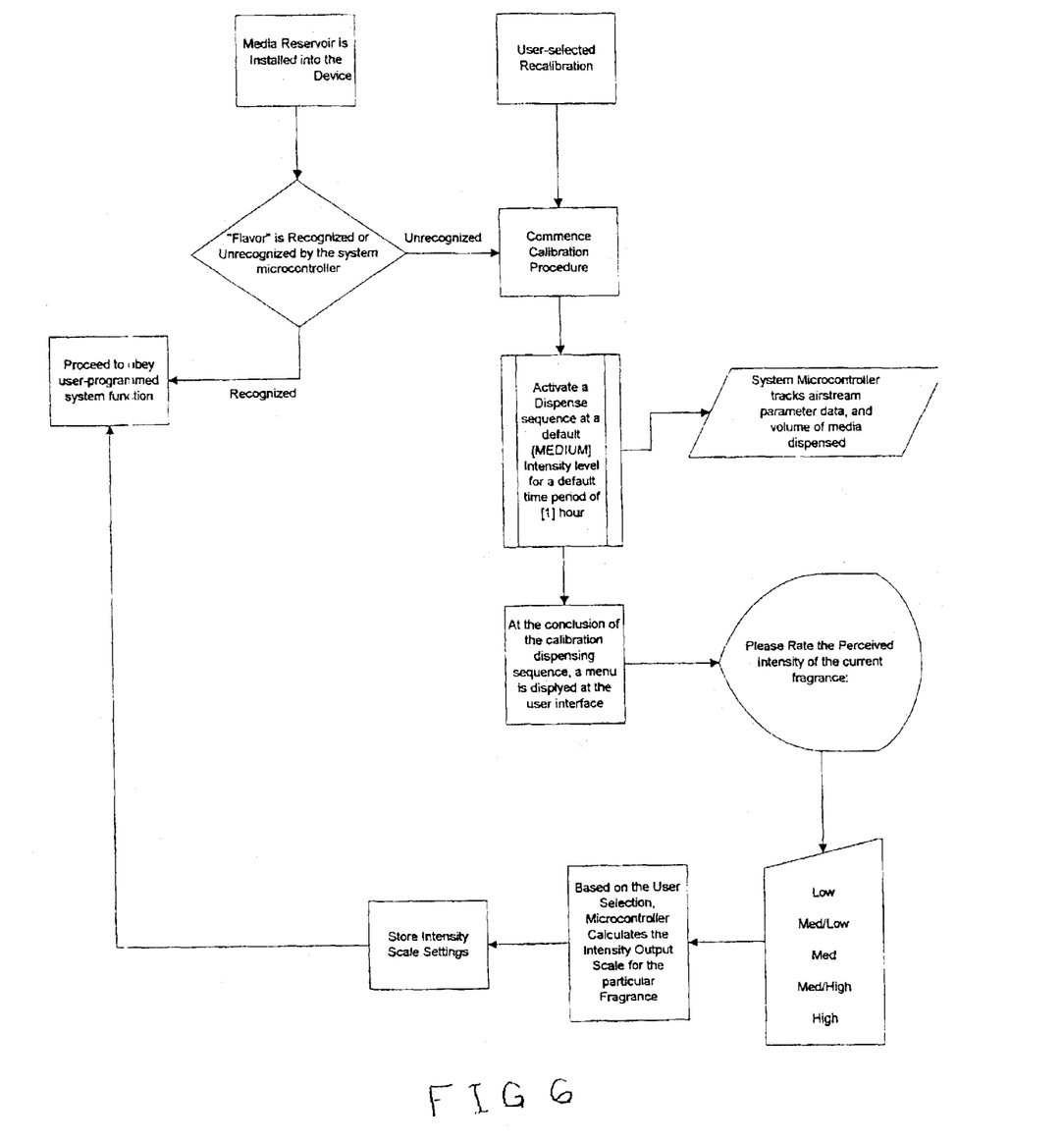
FIG. 6 is a logic block diagram of the user calibrated concentration level selection system.

Once the user has calibrated the output intensity scale for a particular fragrance (or other medium) the system will apply that scale whenever that fragrance (or medium) is recognized. "Recognition" may be implemented, as described earlier herein, by incorporation in each media reservoir of machine readable indicia such as a bar code, magnetic strip, holographic symbol or RFID tag (as commonly used in retail stores for security purposes). The user may re-calibrate at any time, and the system will overwrite the former scale with the newly chosen one. The logic block diagram of FIG. 6 illustrates the sequence of steps in the calibration procedure wherein the user provides inputs based on that user's perceived (desired) intensity of the medium which is dispensed at the default level for a predetermined (default) time period.

Functional Description

Figure 4:
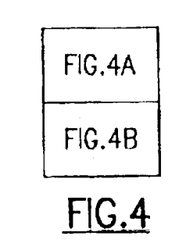
FIG. 4 is a logic block diagram of the system controls through which materials are dispensed into the HVAC air stream in response to the user-defined program inputs.
Figure 4A:
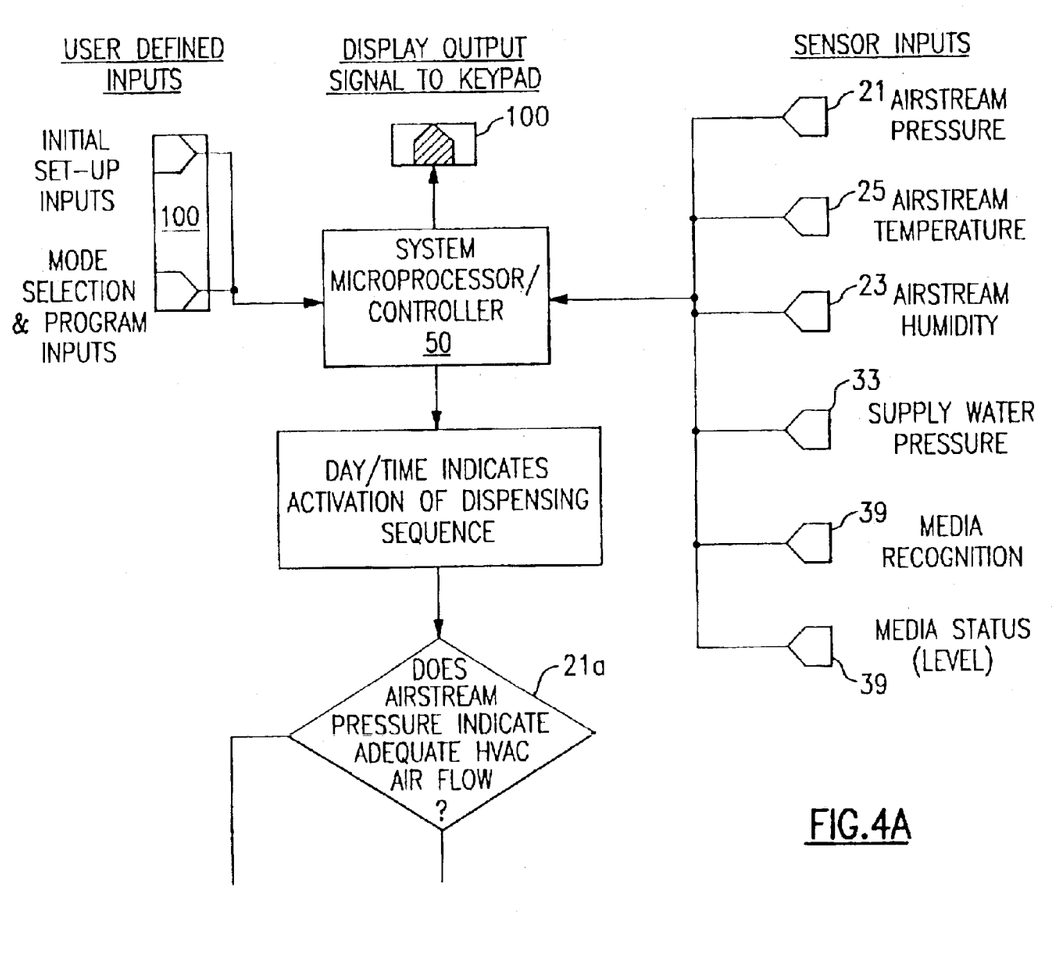
Figure 4B:
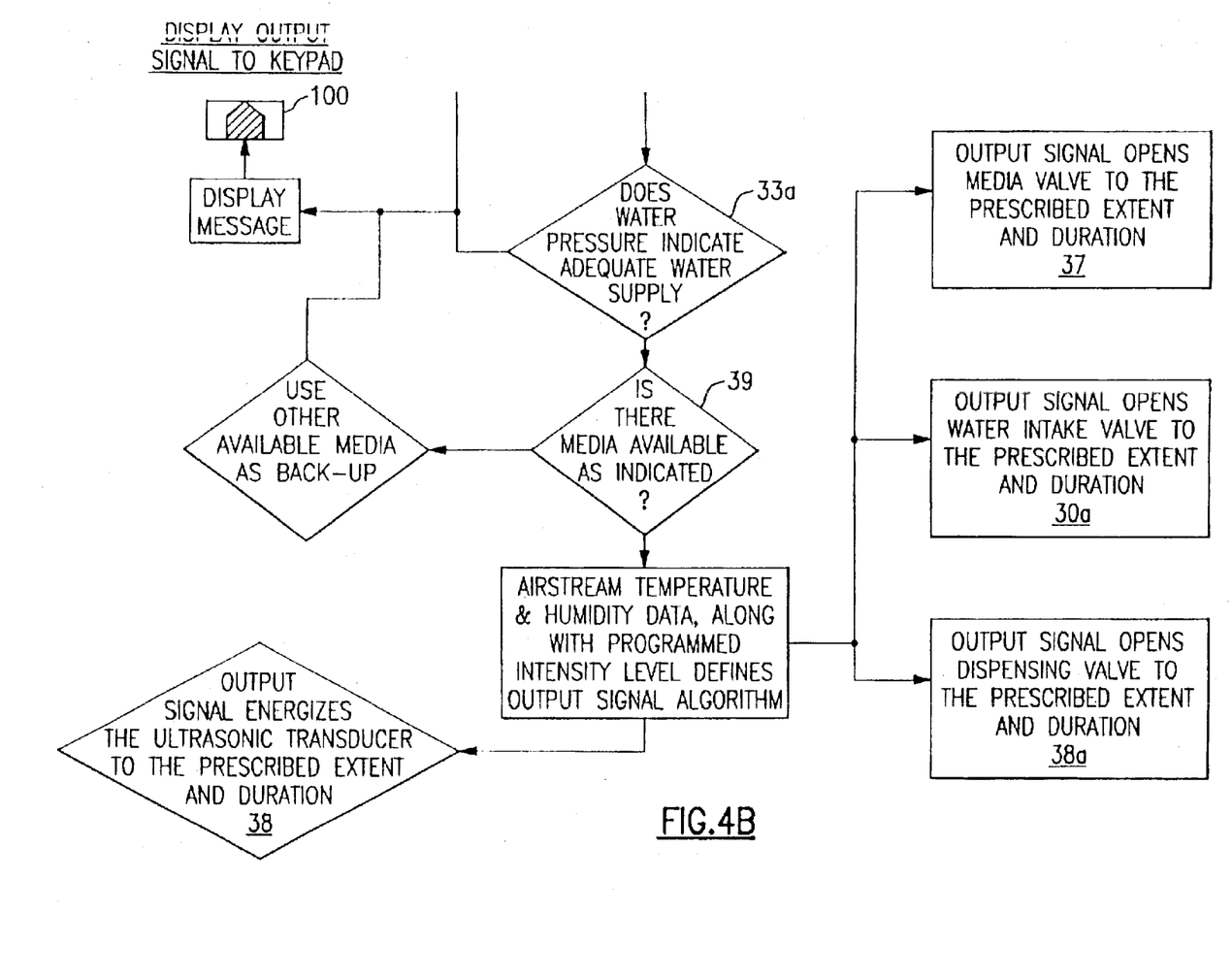

Referring now to FIG. 4, the user inputs the initial information into the system central processor 50 through the keypad/display unit 100 in the manner previously described, selects the mode of operation and programs the system as desired. The temperature sensor 25, humidity sensor 23, flow sensor 21, media sensors 39a, 39b, and 39c, and water supply sensor 33a all provide their respective input signals to the system central processor 50. The keyboard/display 100 shows the status of the informational inputs. If the program cycle inputs, the operational sensor inputs and time of operation call for an activation of a dispensing sequence, dispensing operation is initiated and the keypad/display 100 shows that the system is dispensing as instructed. The selected media dispensing valve 36a, 36b or 36c is opened the prescribed extent and duration. The water intake control valve 30 is opened allowing water and the selected medium to mix in the dilution manifold 34. The dispensing control valve 38 is opened and the dispenser 16 is actuated for a time period determined by the parameters of the ambient air moving through the air duct 11. The input from the ambient air flow sensors 21, 23 and 25 coupled to the system central processor 50 prevent the system from dispensing media at a level beyond the capacity of the air stream flow to move the dispensed medium through the HVAC system.

Referring to FIG. 6, upon installation of a media reservoir the indicia thereon is read to indicate presence of the reservoir and identity of the medium. If the medium is recognized as one for which user-programmed functional data has previously been entered, the system proceeds to operate according to such instructions. Otherwise, the user performs, via the keypad data entry, the necessary input instructions to permit the system to operate at a default intensity level. After operation at that level for a predetermined time period, the user is prompted to enter the perceived concentration level. Stated another way, the user enters a level of intensity rating the concentration during the default period relative to the concentration which the user would prefer. This action serves to shift the concentration algorithm in the manner illustrated in FIG. 5A.

It will be understood that, although the invention has been described as having a diffuser and various sensors mounted in an air flow plenum of a heating, ventilating and/or air conditioning system, it could instead be incorporated in a console or table top humidifier located in the occupied living space with the diffuser discharging directly into the living space.

While this invention has been described in the specification and illustrated in the drawings with reference to a preferred embodiment, the structure of which has been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

What is claimed is:

1. A user-programmable media dispensing system with user-calibrated intensity scale comprising:

a. a supply source of at least one medium for dispensing into an occupied space;

b. a supply source of water for mixture with said medium to provide a solution containing a specified percentage of said medium at each of a plurality of intensity levels;

c. dispensing means for introducing said solution into said air stream;

d. a central processor for receiving input signals and generating output signals including an output signal initiating a default operation of said dispensing means to dispense said solution at a predetermined one of said intensity levels; and e. data entry/display means for selective operation by a user to provide at least some of said input signals to said central processor for changing said default operation of said dispensing means, including a plurality of signals respectively corresponding to a plurality of scales of said intensity levels, each of said scales representing a percentage of said medium in said solution at each of said plurality of intensity levels.

2. The media dispensing system of claim 1 wherein source of said medium is a media reservoir, and wherein said system includes a plurality of said reservoirs, each containing a different medium.

3. The media dispensing system of claim 2 wherein each of said reservoirs has associated therewith a unique one of said input signals, whereby said central processor is informed of the identity of the media in said reservoirs.

4. The media dispensing system of claim 1 wherein said central processor is pre-programmed with a concentration algorithm for said at least one medium establishing a predetermined scale, representing a plurality of percentages of said medium in said solution at each of a plurality of discrete steps between lowest and highest.

5. The media dispensing system of claim 4 wherein at least one of said input signals from said data entry/display means to said central processor changes said concentration algorithm to shift from said predetermined scale to a preferred scale the percentages of said medium at each of said discrete steps.

6. The media dispensing system of claim 5 and further including a plurality of sources of supply corresponding to a plurality of different media and wherein said central processor is pre-programmed with a unique concentration algorithm for each of said different media.

7. The media dispensing system of claim 6 and further including a plurality of media sensors respectively coupled between said plurality of sources of supply and said central processor to provide input signals to said central processor corresponding to the identity of each of said media.

8. The media dispensing system of claim 5 wherein said data entry/display includes means for selective user operation to permit selection of a number of said preferred scales equal to the number of said discrete steps.

9. The media dispensing system of claim 8 wherein the number of said preferred scales and of said discrete steps is five.

10. A user-programmable media dispensing system with user-calibrated intensity scale comprising:

a. dispensing means actuable in response to a dispenser activating control signal to discharge a quantity of a medium in aqueous solution into an occupied space;

b. a dispensing system central processor coupled to said dispensing means and generating a dispenser activating control signal to said dispensing means in response to instruction input signals coupled to said central processor from user-programmable data entry;

c. user-programmable data entry coupled to said dispensing system central processor for entry of user-generated instructions and coupling said user-generated instructions as instruction input signals to said dispensing system central processor for generating said dispenser activating control signals to actuate said dispensing means;

d. said central processor being pre-programmed with a default concentration algorithm according to which the percentage of said medium in said aqueous solution is established at each of a plurality of steps between lowest and highest; and e. said data entry providing, upon user actuation, input signals to said central processor for changing said default concentration algorithm to a preferred concentration algorithm.

11. The media dispensing system of claim 10 wherein said dispensing means includes a plurality of dispensing media containing reservoirs coupled in fluid communication with a media dispenser, and wherein said central processor is pre-programmed with a unique concentration algorithm for the particular medium contained in each of said plurality of reservoir.

12. The media dispensing system of claim 11 wherein said media dispenser is positioned in the air stream of a central or zoned forced-air heating, ventilating and air-conditioning system for dispensing said solution into said air stream at concentrations determined by said preferred concentration algorithm.

13. The media dispensing system of claim 12 and further including air stream sensor means positioned in said air stream and coupled to said central processor for generating ambient-air-determined control signals to said central processor, and wherein said dispenser activating control signal is further responsive to said ambient-air-determined control signals.

14. The media dispensing system of claim 13 wherein said air stream sensor means includes at least one of:

a temperature sensor for generating a control signal responsive to the air stream temperature, a humidity sensor for generating a control signal responsive to the air stream relative humidity, and an air pressure-airflow sensor for generating a control signal responsive to the air stream air pressure/airflow.

15. The media dispensing system of claim 11 wherein each of said plurality of reservoirs includes a media reservoir sensor coupled to said central processor for generating a signal thereto responsive to the amount of media contained therein.

16. The media dispensing system of claim 15 wherein each of said media reservoir sensors generates a signal to said central processor responsive to the presence of said reservoir in the dispensing system and the identity of the particular medium contained therein.

\* \* \* \* \*